United States Patent
Meiler et al.

(10) Patent No.: US 10,327,730 B2
(45) Date of Patent: Jun. 25, 2019

(54) AUTHENTICATION FOR X-RAY IMAGING COMPONENTS

(71) Applicant: VAREX IMAGING CORPORATION, Salt Lake City, UT (US)

(72) Inventors: Michael Meiler, Draper, UT (US); Steven Emmett Hebeler, Salt Lake City, UT (US)

(73) Assignee: VAREX IMAGING CORPORATION, Salt Lake City, UT (US)

(*) Notice: Subject to any disclaimer, the term of this patent is extended or adjusted under 35 U.S.C. 154(b) by 110 days.

(21) Appl. No.: 15/292,435

(22) Filed: Oct. 13, 2016

(65) Prior Publication Data

US 2018/0103923 A1 Apr. 19, 2018

(51) Int. Cl.
- *A61B 6/00* (2006.01)
- *G06F 21/30* (2013.01)
- *A61B 6/03* (2006.01)

(52) U.S. Cl.
CPC ............ *A61B 6/58* (2013.01); *A61B 6/4417* (2013.01); *A61B 6/4494* (2013.01); *A61B 6/566* (2013.01); *G06F 21/30* (2013.01); *A61B 6/032* (2013.01)

(58) Field of Classification Search
None
See application file for complete search history.

(56) References Cited

U.S. PATENT DOCUMENTS

| | | | |
|---|---|---|---|
| 7,766,549 B2 | 8/2010 | Flukiger et al. | |
| 2004/0171935 A1 | 9/2004 | Van Creveld et al. | |
| 2006/0156415 A1* | 7/2006 | Rubinstein | G06F 21/445 726/27 |
| 2008/0230608 A1 | 9/2008 | Lallemang | |
| 2009/0080621 A1* | 3/2009 | Flukiger | A61B 6/00 378/207 |
| 2015/0296619 A1 | 10/2015 | Rooyakkers et al. | |

FOREIGN PATENT DOCUMENTS

| | | |
|---|---|---|
| JP | 2013063190 A | 4/2013 |
| JP | 2017000233 A | 1/2017 |

OTHER PUBLICATIONS

Extended European Search Report dated Feb. 5, 2018, in related European Patent Application No. 17 19 5713 (6 pages).

\* cited by examiner

*Primary Examiner* — Hoon K Song (57) ABSTRACT

A communication channel for an X-ray imaging system may operatively couple a first imaging component to a second imaging component. The communication channel may include a first connector configured to couple to the first imaging component, a second connector configured to couple to the second imaging component, and a first authentication module configured to authenticate with the second imaging component.

23 Claims, 5 Drawing Sheets

AUTHENTICATION FOR X-RAY IMAGING COMPONENTS

BACKGROUND

The present disclosure generally relates to X-ray imaging systems, including embodiments relating to identifying and/or authenticating components of X-ray imaging systems to verify interoperability.

Computed tomography (CT) or X-ray imaging systems typically include an X-ray tube, a detector, and a support structure, such as a gantry, for the X-ray tube and the detector. In operation, an imaging table, on which a patient or object is positioned, is located between the X-ray tube and the detector. A generator provides power and/or timing signals to the X-ray tube. The X-ray tube emits radiation, such as X-rays, toward the object. The radiation passes through the object on the imaging table and impinges on the detector. As radiation passes through the object, internal structures of the object cause spatial variances in the radiation received at the detector. The detector receives the radiation and transmits data representative of the received radiation. The system translates the radiation variances into an image, which may be used to evaluate the internal structure of the object. The object may include, but is not limited to, a patient in a medical imaging procedure and an inanimate object in a package scanner. X-ray imaging systems may include one or more control systems configured to communicate with and/or operate components within the system, such as the X-ray tube, the detector, the gantry, the imaging table and/or other components.

The claimed subject matter is not limited to embodiments that solve any disadvantages or that operate only in environments such as those described above. This background is only provided to illustrate examples of where the present disclosure may be utilized.

SUMMARY

The present disclosure relates to devices and methods that facilitate identifying and/or authenticating components of X-ray imaging systems to verify interoperability.

In one example embodiment, a communication channel operatively couples a first imaging component of an X-ray imaging system to a second imaging component of the X-ray imaging system. The communication channel may include a first connector configured to couple to the first imaging component, a second connector configured to couple to the second imaging component, and a first authentication module configured to authenticate with the second imaging component. The first imaging component may include a controller configured to operate or communicate with the second imaging component, and the second imaging component may include an X-ray tube, a generator, and/or an X-ray detector. The first authentication module may be at least partially positioned within a housing defined by the first connector. A first tamper avoidance device may be associated with the first authentication module and configured to prevent removal of the first authentication module from the first connector.

In some configurations, a cable may extend between the first connector and the second connector to operatively couple the first imaging component to the second imaging component. The first authentication module may be coupled to the cable. In other configurations, a wireless communication link may extend between the first connector and the second connector to operatively couple the first imaging component to the second imaging component.

A second authentication module may be associated with the second imaging component. The first authentication module may authenticate with the second imaging component via the second authentication module. A second tamper avoidance device may be associated with the second authentication module. The second tamper avoidance device may be configured to prevent removal of the second authentication module from the second imaging component. The first authentication module and the second authentication module may implement an authentication protocol that is compliant with at least one of the Advanced Encryption Standard (AES) or the Triple Data Encryption Algorithm (3DES) authentication standard. The second authentication module may include second imaging component data that uniquely corresponds to the second imaging component. The second imaging component may be an X-ray tube, and the second imaging component data may include serial number, part number, batch number, lot number, model number, manufacturing date, manufacturing location, country of origin, application code version, and/or bootloader version.

In another embodiment, a method may operatively couple a first imaging component of an X-ray imaging system to a second imaging component of the X-ray imaging system. The method may include challenging a first imaging component to authenticate, receiving a first imaging component response as a result of the first imaging component challenge, challenging a communication channel coupled to the first imaging component to authenticate, receiving a communication channel response as a result of the communication channel challenge, and authenticating the first imaging component if the first imaging component response matches the communication channel response.

In some configurations, the first imaging component may include a controller configured to operate or communicate with the second imaging component, and the second imaging component may include an X-ray tube, a generator, and/or an X-ray detector. The first imaging component response may include first imaging component data that uniquely corresponds to the first imaging component. The first imaging component data may include serial number, part number, batch number, lot number, model number, manufacturing date, manufacturing location, country of origin, application code version, and/or bootloader version.

The first imaging component response and the communication channel response may be received at the second imaging component, and the step of authenticating may be performed at the second imaging component. The method may include encrypting the first imaging component challenge, the first imaging component response, the communication channel challenge, and/or the communication channel response. The method may include decrypting the first imaging component challenge, the first imaging component response, the communication channel challenge, and/or the communication channel response. The method may include communicating imaging data or control signals over the communication channel after the first imaging component is authenticated.

In another example, a system may include a first imaging component and a communication channel. The first imaging component may include an authentication module. The communication channel may include a first connector, a second connector, and a channel authentication module. The communication channel may communicatively couple the first imaging component to the second imaging component. The first connector may be configured to be coupled to the first imaging component. The second connector may be configured to be coupled to the second imaging component. The channel authentication module may be configured to authenticate with the first imaging component authentication module.

In some configurations, the communication channel may include a cable extending between the first connector and the second connector. The channel authentication module may be at least partially positioned within a housing formed by the second connector. The first imaging component authentication module and the channel authentication module may include first imaging component data that uniquely corresponds to the first imaging component.

This Summary introduces a selection of concepts in a simplified form that are further described below in the Detailed Description. This Summary is not intended to identify key features or essential characteristics of the claimed subject matter, nor is it intended to be used as an aid in determining the scope of the claimed subject matter.

DETAILED DESCRIPTION

Reference will be made to the drawings and specific language will be used to describe various aspects of the disclosure. Using the drawings and description in this manner should not be construed as limiting its scope. Additional aspects may be apparent in light of the disclosure, including the claims, or may be learned by practice.

Computed tomography (CT) or X-ray imaging systems typically include an X-ray tube, a detector, and a support structure, such as a gantry, for the X-ray tube and the detector.

During the operating lifespan of an X-ray imaging system, certain components may be repaired or replaced to ensure the X-ray imaging system continues to operate properly. For example, an imaging component such as an X-ray tube, a generator, and/or a detector may be repaired or replaced to maintain proper operation of the X-ray imaging system.

When a new component, such as a replacement X-ray tube, generator, and/or detector is introduced into the X-ray imaging system, it may be important to identify the component and verify that the proper component is being coupled to the system. Similarly, if a component is removed from the X-ray imaging system, for example, to be repaired, it may be important to verify that the proper component is returned to the X-ray imaging system. Additionally, it may be important to verify that components introduced into the X-ray imaging system are functionally compatible with the other components of the system.

Since each component may have unique operational characteristics, verifying that a replacement component is compatible with the X-ray imaging system may facilitate safe operation of the X-ray imaging system to produce suitable quality images. In contrast, introducing an improper component into the X-ray imaging system may result in unsafe operation or poor image quality. For example, using incompatible X-ray tubes in an X-ray imaging system can result in punctures, anode meltdown, overheating and safety issues such as dosimetric errors that can lead to overexposure of the patient to radiation. In another example, using incompatible X-ray tubes may result in poor image quality that may not adequately represent diseases or abnormalities in a patient, which may lead to misdiagnosis, false positives, and/or missed detections. Similarly, using incompatible generators, detectors or other imaging components may also lead to unsafe operation or poor image quality. Confirming that components (e.g., X-ray tubes, generators, detectors, etc.) introduced into the X-ray imaging system are compatible with the other portions of the X-ray imaging system may help avoid unsafe operation and issues associated with poor image quality.

In some circumstances, a component (e.g., X-ray tube, generator, detector, etc.) may be replaced with a third party component that is not fully compatible with a given X-ray imaging system. Third party components may be inexpensive, low-quality alternatives with poor imaging characteristics. For example, third party X-ray tubes may create improper radiation outputs, focal spot sizes, and other imaging issues. In some circumstances, use of third party components may result in unsafe operation of X-ray imaging systems. In addition, the use of third party components may result in decreased revenue for original equipment manufacturers (OEM) of X-ray imaging systems and/or component manufacturers. Using incompatible third party components may also lead to warranty issues for the customer or the manufacturer.

In some jurisdictions, operators of X-ray imaging systems may be required to comply with imaging quality standards, which require, for example, regular quality assessments (e.g., daily, weekly, monthly, etc.) to ensure X-ray imaging systems maintain proper operation. However, in other jurisdictions regular quality assessments are not required and may not be performed. In such circumstances, issues related to unsafe operation of X-ray imaging systems or poor image quality may persist without being detected for longer periods of time. In turn, patients may be exposed to greater risks of misdiagnosis, false positives, and/or missed detections.

The disclosed embodiments may facilitate identifying and/or authenticating components of X-ray imaging systems (e.g., X-ray tube, generator, detector, etc.) to verify interoperability. This may prevent incompatible components from being used in X-ray imaging systems, thereby facilitating safe operation of X-ray imaging system and production of suitable quality images for patient diagnosis. The disclosed embodiments may ensure that components introduced into an X-ray imaging system are compatible with the other components of the X-ray imaging system. Moreover, the identification and authentication process may be automatic and transparent to operators of the X-ray imaging system, to help ensure suitable image quality and safe operation without requiring regular quality assessments.

The disclosed embodiments may facilitate manufacturers of X-ray imaging systems to help ensure high quality, compatible components (e.g., X-ray tubes, generators, detectors, etc.) are used with their X-ray imaging systems. In addition, manufactures may prevent third party components from being used with their X-ray imaging systems, to avoid issues associated with low-quality third party components such as poor imaging characteristics, unsafe operation, warranty issues, and decreased revenue for manufacturers of X-ray imaging systems and/or components.

The present disclosure includes low-cost solutions that may be implemented in cost-sensitive markets. For example, embodiments for identifying and/or authenticating components may be implemented without significantly increasing the cost of the components or the X-ray imaging system. This may facilitate ensuring that proper, high-quality components are implemented in X-ray imaging systems without significantly increasing costs to the customer.

In addition, the disclosed embodiments may permit components (e.g., X-ray tubes, generators, detectors, etc.) to be uniquely identified. This may permit differentiation between different components having unique characteristics. For example, components may be identified and differentiated based on unique identifying information such as serial number, part number, batch number, lot number, model number, manufacturing date, manufacturing location, country of origin, application code version, and/or bootloader version. In some embodiments, this information may be provided to a control component(s) so it may be adjusted based on the unique characteristics of the imaging components.

The disclosed embodiments may permit the X-ray imaging system to take steps in response to a component being authenticated and/or failing to authenticate. For example, the X-ray imaging system may boot up and/or operate normally in response to a successful authentication of a component (or multiple components). In another example, the X-ray imaging system may notify the operator of the system that a non-approved component is connected to the system in response to a failed authentication. In yet another example, the X-ray imaging system may cease operating in response to a failed authentication to ensure patient and operator safety. In some circumstances, the response taken by the X-ray imaging system may be determined by the manufacturer and/or may depend on legal requirements in the jurisdiction where the customer is located.

Although imaging components such as X-ray tubes, generators, detectors are examples of some components of an X-ray imaging system, the described concepts may be implemented to identify and/or authenticate any suitable components of X-ray imaging systems. For example, embodiments may be implemented to identify and/or authenticate control system components (e.g., tube control units), heat exchangers, and/or auxiliary equipment of the X-ray imaging system.

Figure 1:
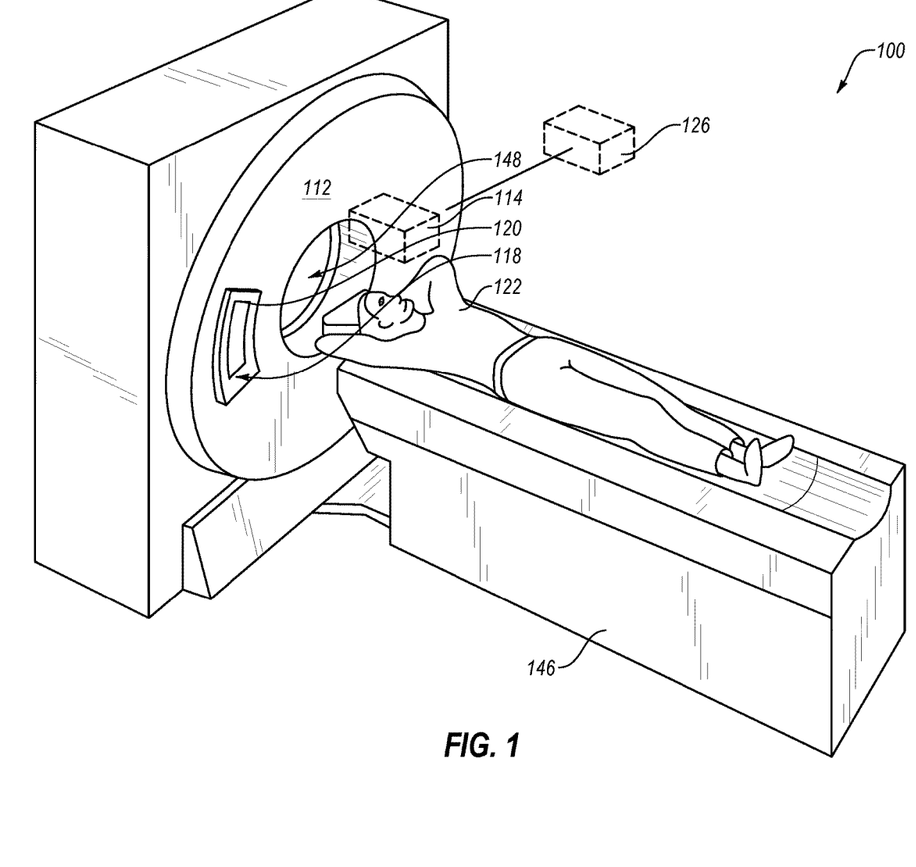
FIG. 1 is a perspective view of one example of an X-ray imaging system.

FIG. 1 is a perspective view of an embodiment of an X-ray imaging system 100 that may be used to acquire image data and process, display, and/or analyze the image data. In some circumstances, the system 100 may be referred to as a computed tomography (CT) or X-ray imaging system. The system 100 is an example of an operating environment where the concepts described in this disclosure may be implemented, but it is not limiting. The concepts described may be implemented in other X-ray imaging systems.

Referring to FIG. 1, the system 100 includes a gantry 112 with an X-ray source assembly 114 that projects X-rays toward a collimator or a detector assembly 118 on an opposite side of the gantry 112. The system 100 may include an actuating table 146 to receive and position a patient 122 or an object to be scanned. The actuating table 146 may move to position a patient 122 to be analyzed by the system 100. Specifically, the actuating table 146 may move the patient 122 at least partially through an opening 148 of the gantry 112 such that X-rays from the X-ray source assembly 114 pass through the patient 122 and are received by the detector assembly 118 to obtain information about the patient 122. The X-ray source assembly 114 may include an X-ray tube to generate X-rays. The detector assembly 118 may include a plurality of detectors 120 to detect x-rays that pass through the patient 122 positioned on an actuating table 146.

The X-ray source assembly 114 may be operatively coupled to a controller such as a system control unit 126. In general, the system control unit 126 may interface with and control various components of the system 100. In addition, the system control unit 126 may interface with the X-ray source assembly 114 so as to provide, for example, control signals to the X-ray source assembly 114. In some configurations, a generator (not shown) may provide, for example, power and/or timing signals to the X-ray source assembly 114. The system control unit 126 may interface with the generator so as to provide, for example, control signals to the generator.

During a scan of the patient 122 to acquire X-ray projection data, the actuating table 146 may position a portion of the patient 122 to be analyzed at least partially through the opening 148 of the gantry 112. During operation, the gantry 112 and the components mounted thereon may rotate about a center of rotation, and the X-ray source assembly 114 may emit X-rays that travel through the patient 122 to the detector assembly 118. The gantry 112 and the actuating table 146 may be operatively coupled to the system control unit 126. Rotation of the gantry 112 and actuation of the actuating table 146 may be at least partially controlled by the system control unit 126.

The system control unit 126 may receive the digital signals representative of the radiation received at the detector assembly 118, which may be processed or stored in memory. The system control unit 126 may receive commands and scanning parameters from an operator via a console (not shown) that has some form of operator interface, such as a display, keyboard, mouse, or any other suitable interface components. An associated display (not shown) may allow the operator to observe images and other data from the system control unit 126. The operator may make adjustments to the operation of the X-ray assembly 114 via the system control unit 126, which is operably interfaced with the X-ray assembly 114. In some configurations, the operator may make adjustments to the operation of a generator (not shown) to provide, for example, power and/or timing signals to the X-ray source assembly 114.

Although the system 100 illustrated is configured to analyze the patient 122, in alternative configurations the system 100 may be configured to analyze a sample or analyte rather than a patient. In such circumstances, the actuating table 146 and/or the gantry 112 may be adapted based on the size and shape of the sample to be analyzed.

Figure 2:
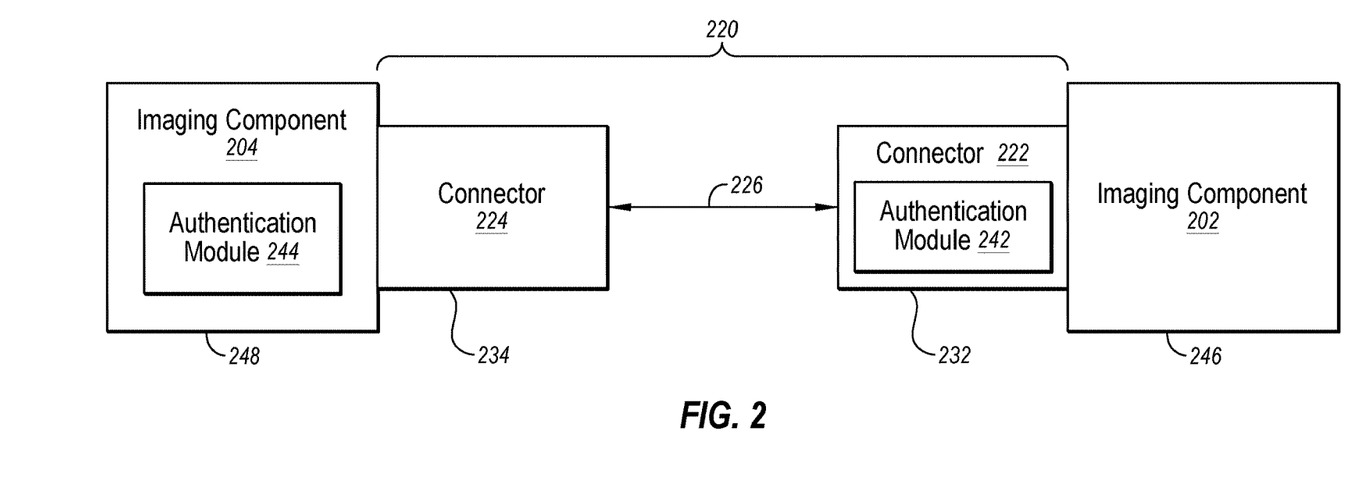
FIG. 2 is a schematic diagram of a communication channel that may be implemented in the X-ray imaging system illustrated in FIG. 1.

FIG. 2 is a schematic diagram of a portion of the system 100 illustrating a communication channel 220 that may be implemented in the system 100. As illustrated, the communication channel 220 operatively couples a first imaging component 202 to a second imaging component 204.

In the illustrated configuration, a first authentication module 242 is associated with the communication channel 220 and a second authentication module 244 is associated with the imaging component 204. The imaging component 202, the authentication module 242, and/or the authentication module 244 may be configured to identify and/or authenticate the imaging component 204 with the imaging component 202, as will be described in further detail below.

The authentication module 242 and/or the authentication module 244 may include data that indicates whether the imaging component 202 and the imaging component 204 are functionally matched to one another. For example, the authentication module 242 and/or the authentication module 244 may each include a unique key. In some configurations, the key included in the authentication module 242 may be unique to the imaging component 202 or the communication channel 220. Additionally or alternatively, the key included in the authentication module 244 may be unique to the imaging component 204. In some configurations, the same key may be used for all components produced by a certain manufacturer. In such configurations, the authentication module 242 and the authentication module 244 may each include the same key, specific to the manufacturer of the imaging component 202 and the imaging component 204. In some configurations, the key may be combined with data unique to the imaging component 202 and/or the imaging component 204.

As illustrated, the communication channel 220 may include a first connector 222 configured to couple to the imaging component 202, and a second connector 224 configured to couple to the imaging component 204. A communication link 226 extends between the connector 222 and the connector 224. The communication link 226 communicatively couples the imaging component 204 to the imaging component 202.

The connector 222 may include a housing 232 partially or entirely surrounding portions of the connector 222. As illustrated, the authentication module 242 is at least partially positioned within the housing 232 defined by the first connector 222. Similarly, the connector 224 may include a housing 234 partially or entirely surrounding portions of the connector 224.

As mentioned above, the connector 222 may be configured to couple to the imaging component 202. The connector 222 may mechanically and communicatively couple the communication channel 220 to the imaging component 202. In some configurations, the connector 222 may removably couple to the imaging component 202. For example, the connector 222 may include a plug configured to mate with a corresponding socket of the imaging component 202, or vice versa. In other configurations, the connector 222 may be permanently or semi-permanently coupled to the imaging component 202. For example, the connector 222 may be permanently affixed to a housing 246 of the imaging component 202 in a manner such that removal of the connector 222 from the housing 246 may damage either the imaging component 202 or the connector 222 (e.g., permanent fasteners, adhesive, tamper-proof screws, etc.). Thus, in some configurations, the connector 222 cannot be removed from the imaging component 202 without damaging the imaging component 202 or the connector 222. The authentication module 242 of the connector 222 may be communicatively coupled to the imaging component 202 via the connector 222.

The connector 224 may be configured to couple to the imaging component 204. The connector 224 may mechanically and communicatively couple the communication channel 220 to the imaging component 204. In some configurations, the connector 224 may be permanently or semi-permanently coupled to the imaging component 204. For example, the connector 224 may be permanently affixed to a housing 248 of the imaging component 204 in a manner such that removal of the connector 224 from the housing 248 may damage either the imaging component 204 or the connector 224 (e.g., permanent fasteners, adhesive, tamper-proof screws, etc.). Thus, in some configurations, the connector 224 cannot be removed from the imaging component 204 without damaging the imaging component 204 or the connector 224. In other configurations, the connector 224 may removably couple to the imaging component 204. For example, the connector 224 may include a plug configured to mate with a corresponding socket of the imaging component 204, or vice versa. The authentication module 244 may be communicatively coupled to the imaging component 202 via the connector 224, the communication link 226, and the connector 222.

The communication channel 220 may be configured to send analog, digital and/or wireless signals between the imaging component 202 and the imaging component 204. The communication channel 220 includes the communication link 226 extending between the connector 222 and the connector 224 to communicatively couple the imaging component 202 and the imaging component 204. In some configurations, the communication link 226 may be an encrypted link or other secure connection that prevents communications between the imaging component 202 and imaging component 204 from being monitored, intercepted, and/or deciphered. The secure connection may be configured to substantially prevent circumvention of the authentication mechanism provided by the authentication module 242 and/or the authentication module 244.

In some configurations, the communication link 226 may be a cable physically extending between the connector 222 and the connector 224, thereby operatively coupling the imaging component 202 to the imaging component 204. In such configurations, the authentication module 242 may be coupled to the cable. The cable may be any suitable cable, such as an electrically cable capable of transmitting electrical signals, or an optical cable capable of transmitting optical signals.

In other configurations, the communication link 226 may be a wireless communication link wirelessly coupling the imaging component 202 to the imaging component 204. The wireless communication link may extend between the connector 222 and the connector 224, thereby operatively coupling the imaging component 202 to the imaging component 204. In such configurations, the connector 222 may include a first wireless transmitter and a first wireless receiver 222, and the connector 224 may include a second wireless transmitter and a second wireless receiver. The first wireless transmitter may be configured to wirelessly transmit data to the second wireless receiver, and the second wireless transmitter may be configured to wirelessly transmit data to the first wireless receiver. In an example, the wireless communication link may use WiFi, Institute of Electrical and Electronics Engineers (IEEE) 802.11 standard, Bluetooth, or IEEE 802.15 wireless communication standard.

As mentioned above, the authentication module 242 may be positioned at least partially inside of the housing 232 of the connector 222. The authentication module 242 may further include a tamper avoidance device configured to prevent or discourage removal of the authentication module 242 from the connector 222. In some configurations, the tamper avoidance device may prevent the authentication module 242 from being removed from the connector 222 without damaging either the connector 222 or the authentication module 242.

In some configurations, the authentication module 244 may be permanently affixed to a housing 248 of the imaging component 204. In other configurations, the authentication module 244 may be positioned at least partially inside of the housing 248. The authentication module 244 may include a tamper avoidance device configured to prevent or discourage removal of the authentication module 244 from the imaging component 204. In some configurations, the tamper avoidance device may prevent the authentication module 244 from being removed from the imaging component 204 (e.g., the housing 248) without damaging either the imaging component 204 or the authentication module 244.

The authentication module 242 and the authentication module 244 may be configured to identify and/or authenticate the imaging component 204. For example, the authentication module 242 may authenticate with the imaging component 204 via the authentication module 244. In some configurations, authentication may be performed at the imaging component 202. In other configurations, authentication may occur between the authentication module 242 and the authentication module 244. Authentication will be discussed in further detail below.

In other configurations, the authentication module 242 may be associated with the imaging component 202 rather than the communication channel 220. In such configurations, the authentication module 242 may be removably or permanently coupled to the imaging component 202. For example, the authentication module 242 may be removably or permanently coupled to the housing 246. In another example, the authentication module 242 may be at least partially positioned inside of the housing 246 defined by the imaging component 202.

The imaging component 202 and the imaging component 204 may be any suitable components of an X-ray imaging system, such as the system 100 described with respect to FIG. 1. For example, the imaging component 202 may be a controller configured to communicate with and/or operate the imaging component 204, such as the system control unit 126, and the imaging component 204 may be an X-ray tube of the X-ray source assembly 114, a generator, and/or an X-ray detector of the detector assembly 118. In such configurations, the system control unit 126 may be configured to authenticate and/or identify the X-ray tube, the generator, and/or the X-ray detector. In another example, the imaging component 204 may be an X-ray tube and the imaging component 202 may be a generator configured to power the X-ray tube. In such configurations, the generator may be configured to authenticate and/or identify the X-ray tube. In further configurations, any suitable component of the system 100 may be configured to authenticate another suitable component of the system 100. For example, the components may include a control system component (e.g., tube control unit), a heat exchanger, and/or an auxiliary component of the system 100.

In some configurations, the imaging component 202 transmits control, power and/or timing signals to the imaging component 204, via the communication link 226, to communicate with and/or operate the imaging component 204. For example, the imaging component 202 may transmit control signals to a generator, which in turn provides power and/or timing signals to an X-ray tube. Additionally or alternatively, the imaging component 204 may transmit analog or digital signals representative of received images, via the communication link 226, to the imaging component 202. For example, the imaging component 204 may be a collimator or detector that receives an X-ray beam that has passed through a patient, and transmits signals representative of the X-ray beam to the imaging component 202.

As mentioned above, the imaging component 202, the authentication module 242, and/or the authentication module 244 may be configured to identify and/or authenticate the imaging component 204.

Figure 3:
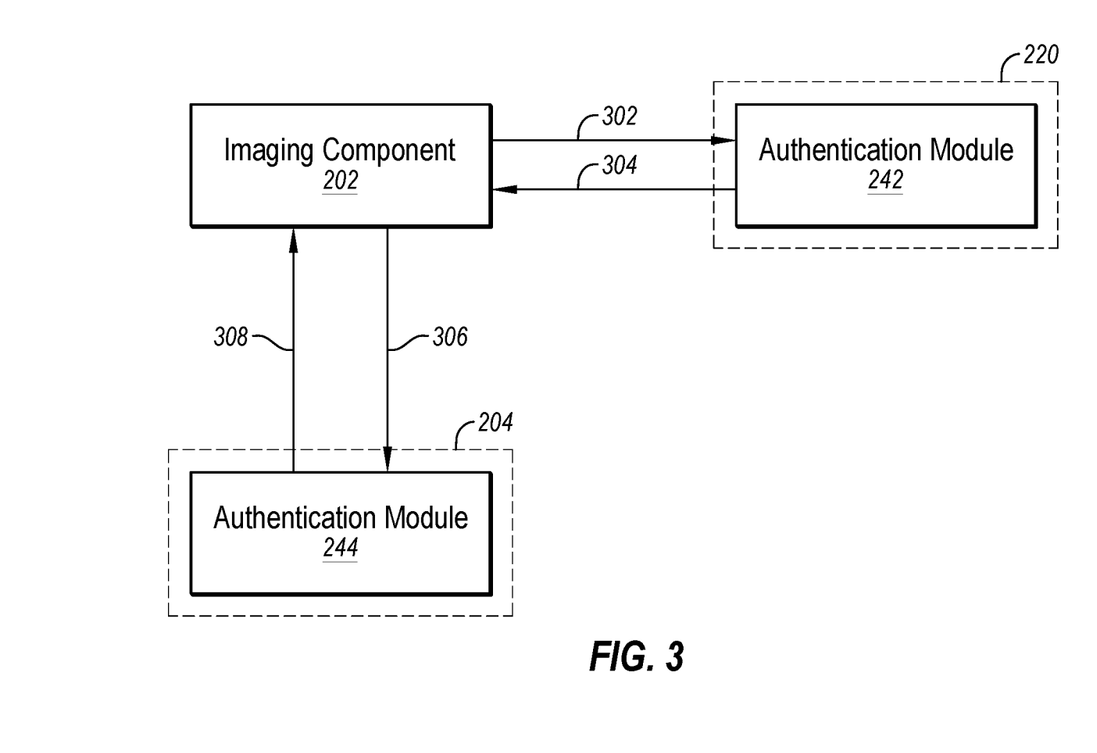
FIG. 3 is a schematic diagram of a portion of the X-ray imaging system illustrated in FIG. 1.

FIG. 3 is a schematic diagram of a portion of the example system 100 including the imaging component 202, the authentication module 242, and the authentication module 244. With reference to FIG. 3, identification and authentication will be discussed in further detail.

As illustrated, the imaging component 202 is communicatively coupled to the authentication module 242 and the authentication module 244. Specifically, the authentication module 242 and the authentication module 244 may communicate with the imaging component 202 via the communication channel 220 (see FIG. 2). In some configurations, the imaging component 202 may include an application programming interface (API) to communicate with the authentication module 242 and the authentication module 244. The authentication module 242 is associated with the communication channel 220, denoted at dashed component 220, and the authentication module 244 is associated with the imaging component 204, denoted at dashed component 204.

Authentication and identification may be performed upon startup of the X-ray imaging system, or at any suitable time during operation. The imaging component 202 may transmit a challenge, denoted at 302, to the authentication module 242. The challenge 302 may include a query or request for authentication information. The challenge 302 may be received at the authentication module 242.

In response to the challenge 302, the authentication module 242 may transmit a response, denoted at 304, to the challenge 302. The response 304 may include authentication information, such as an authentication key, stored on the authentication module 242. The response 304 may be received at the imaging component 202 as a result of the challenge 302.

The imaging component 202 may transmit a challenge, denoted at 306, to the authentication module 244. The challenge 302 may include a query or request for identifying data and/or authentication information. The requested identifying data may uniquely correspond to the imaging component 204. The challenge 306 may be received at the authentication module 244. In response to the challenge 306, the authentication module 244 may transmit a response, denoted at 308, to the challenge 306. The response 308 may include authentication information, such as an authentication key, stored on the authentication module 244. The response 308 may be received at the imaging component 202 as a result of the challenge 306.

In some configurations, the response 304 and/or the response 308 may include imaging component data that uniquely corresponds to the imaging component 204. For example, the imaging component data may include serial number, part number, batch number, lot number, model number, manufacturing date, manufacturing location, country of origin, application code version, and/or bootloader version.

After receiving the response 304 and response 308, the imaging component 202 may compare the response 304 to the response 308. If the response 304 matches the response 308 (or vice versa), the imaging component 202 may authenticate the imaging component 204. If the response 304 does not match the response 308 (or vice versa), the imaging component 202 may fail to authenticate the imaging component 204. Additionally or alternatively, if either the response 304 or the response 308 is not received at the imaging component 202, the imaging component 202 may fail to authenticate the imaging component 204.

In configurations where the response 304 and/or the response 308 includes imaging component data, (e.g., a serial number, etc.) the imaging component 202 may compare the imaging component data to determine whether the response 304 and/or the response 308 includes matching imaging component data. In some configurations, for example, the imaging component 202 may include a list of acceptable serial numbers corresponding to imaging components that are functionally compatible with the imaging component 202 or other components in the system 100.

For example, if the imaging component 202 transmits the challenge 302 and fails to receive a response from the authentication module 242 after a specified amount of time has passed, then the imaging component 202 may fail to authenticate the imaging component 204. In another example, if the imaging component 202 transmits the challenge 306 and fails to receive a response from the authentication module 244 after a specified amount of time passes, then the imaging component 202 may fail to authenticate the imaging component 204.

The imaging component 202, the imaging component 204 and/or the communication channel 220 may be configured not to transfer certain data before the imaging component 202 is authenticated with the imaging component 204. For example, the imaging component 202 may be configured to release or transmit data to communicate with and/or operate the imaging component 204 only after the imaging component 204 is authenticated. In another example, the imaging component 204 may be configured to release or transmit data to the imaging component 202 only after the imaging component 202 is authenticated. This may prevent imaging components from communicating with and/or being operated with other imaging components that are not fully compatible, leading to flawed or potentially dangerous operation of the system 100. This may also prevent third party components from being used with the system 100, thereby avoiding unsafe operation or poor image quality. In some configurations, the system 100 may only be operational after the imaging component 202 and the imaging component 204 are authenticated with one another. If the imaging component 202 and/or the imaging component 204 are successfully authenticated, imaging data or control signals may be communicated between the imaging component 202 and the imaging component 204 over the communication channel 220 (see FIG. 2).

The system 100 may be configured to take steps in response to the imaging component 204 being authenticated and/or failing to authenticate. For example, the imaging component 202 may boot up and/or operate normally in response to a successful authentication of the imaging component 204. In another example, the imaging component 202 may notify the operator of the system 100 that a non-approved component is connected to the system in response to a failed authentication. In another example, the imaging component 202 may notify the manufacturer of the system 100 or a third party that a non-approved component is connected to the system in response to a failed authentication. In yet another example, the imaging component 202 may cease operating in response to a failed authentication of the imaging component 204, or vice versa. Accordingly, the imaging component 202 and/or the imaging component 204 may prevent the system 100 from operating in circumstances where at least one component fails to be authenticated. In some circumstances, the response taken by the imaging component 202 may be determined by the manufacturer and/or may depend on legal requirements in the jurisdiction where the customer is located.

In some configurations, the system 100 may be configured to log information in response to a failed or successful authentication. For example, the system 100 may log the identity of the operator of the system 100 in response to a failed authentication. In another example, the system 100 may log information regarding a non-authenticated imaging component in response to a failed authentication. In some configurations, the system 100 may be configured to permit multiple attempts to authenticate before an authentication failure occurs, or before steps are taken in in response to a failure to authenticate.

In some configurations, the challenge 302, the response 304, the challenge 306, and/or the response 308 may be transmitted over an encrypted link that prevents the communications from being monitored, intercepted, and/or deciphered. The authentication module 242 and the authentication module 244 may implement an authentication protocol that is compliant with at least one of the Advanced Encryption Standard (AES) or the Triple Data Encryption Algorithm (3DES or TDEA) authentication standard. AES (a subset of the Rijndael cipher) uses a symmetric-key algorithm, meaning the same key is used for both encrypting and decrypting the data. DES is also a symmetric-key block cipher. In other configurations, the authentication module 242 and/or the authentication module 244 may implement other suitable authentication protocols, such as public-key encryption (also known as asymmetric key encryption).

The imaging component 202 may encrypt the challenge 302 prior to transmittal to the authentication module 242. Upon receipt of the encrypted challenge 302, the authentication module 242 may decrypt the challenge 302. The authentication module 242 may encrypt the response 304 prior to transmittal to the imaging component 202. Upon receipt of the encrypted response 304, the imaging component 202 may decrypt the response 304.

The imaging component 202 may encrypt the challenge 306 prior to transmittal to the authentication module 244. Upon receipt of the encrypted challenge 306, the authentication module 244 may decrypt the challenge 306. The authentication module 244 may encrypt the response 308 prior to transmittal to the imaging component 202. Upon receipt of the encrypted response 308, the imaging component 202 may decrypt the response 308.

In some configurations, the authentication module 242 and/or the authentication module 244 may include an ATSHA204A authentication chip produced by Atmel, or another suitable authentication chip or module. In other configurations, the authentication module 242 and/or the authentication module 244 may be implemented as a field-programmable gate array (FPGA) or a software module.

In some configurations, the authentication module 242 and/or the authentication module 244 may be configured to withstand the operating conditions of portions of the system 100. For example, the authentication module 242 and/or the authentication module 244 may be configured to withstand operating temperatures, pressure, rotational forces and/or other conditions of the system 100. For example, the authentication module 242 and/or the authentication module 244 may be configured to withstand operating temperatures of at least 40° C., 75° C., and/or 85° C. In another example, the authentication module 242 and/or the authentication module 244 may be configured to withstand g-forces of at least 22 g or 44 g. In yet another example, the authentication module 242 and/or the authentication module 244 may be configured to withstand pressures of at least 70 kPa or 106 kPa.

In some configurations, the authentication module 242 and/or the authentication module 244 may include memory and/or a processor. The memory may include manufacturing data for the imaging component 202 and/or the imaging component 204. The processor may be a microprocessor, field-programmable gate array (FPGA), or similar device or circuit. In some configurations, the processor and/or the memory may be configured to withstand the operating conditions of the system 100.

The disclosed concepts permit the imaging component 204 to be identified prior to operation of the system 100 (see FIG. 1) to ensure that the proper component is being coupled to the system 100. If an imaging component is removed from the system 100, for example, to be repaired, the returned imaging component may be verified before the system 100 is operated.

The disclosed concepts also permit manufacturers and customers to verify that functionally compatible imaging components are used in the system 100 to avoid unsafe operation or poor image quality. This may prevent incompatible components from being used in X-ray imaging systems, thereby facilitating safe operation of the system 100 and production of suitable quality images for patient diagnosis Furthermore, the disclosed concepts may ensure that low-quality third party components are not used in the system 100. Moreover, the identification and authentication process may be automatic and transparent to operators of the X-ray imaging system, to help ensure suitable image quality and safe operation without requiring regular quality assessments.

The disclosed concepts may provide authentication of imaging components of the system 100 that cannot be bypassed. For example, as described above, the disclosed systems include tamper avoidance features such that attempted removal, duplication, or modification of the communication channel 220 or the cable 226 (see FIG. 2) will lead to failed authentication. Similarly, attempts to bypass the communication channel 220, the cable 226, the authentication module 242, and/or the authentication module 244 will also lead to failed authentication because the key or other authentication data is not known. Furthermore, all communications may be communicated over a secure, encrypted connection (see communication link 226 of FIG. 2) to ensure that each message sent through the communication channel 220 is unique and never repeated, so that transmitted messages cannot be read, derived and/or duplicated to circumvent keys or other authentication procedures.

In some configurations, existing imaging components may be retrofitted to implement the concepts described herein. For example, an imaging component may be retrofitted with an authentication module, which may be permanently attached with a tamper avoidance device to ensure the authentication module cannot be removed. The imaging component may be coupled to second imaging component with a communication link that includes a second authentication module. In such configurations, the second imaging component may authenticate the first imaging component using the authentication modules as described herein.

As mentioned above, in some configurations the imaging component 202 may be a controller such as the system control unit 126 and the imaging component 204 may be an X-ray tube of the X-ray source assembly 114 (see FIG. 1).

Figure 4:
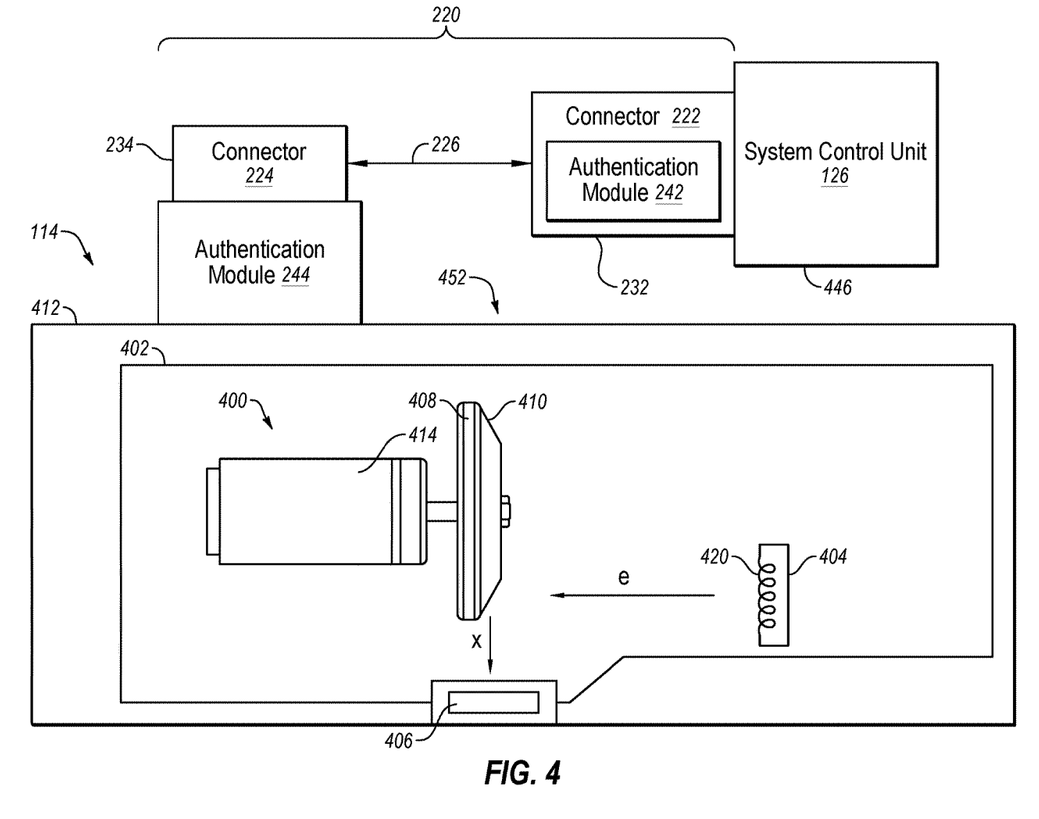
FIG. 4 is another schematic diagram of a portion of the X-ray imaging system illustrated in FIG. 1.

FIG. 4 illustrates an example of such configurations, where the communication channel 220 operatively couples an X-ray tube 452 of the X-ray assembly 114 to the system control unit 126.

In such configurations, the first connector 222 may be configured to couple to the system control unit 126, and the second connector 224 may be configured to couple to the X-ray assembly 114. The communication link 226 extends between the connector 222 and the connector 224 and communicatively couples the system control unit 126 to the X-ray assembly 114.

The connector 222 may mechanically and communicatively couple the communication channel 220 to the system control unit 126. In some configurations, the connector 222 may removably couple to the system control unit 126. For example, the connector 222 may include a plug configured to mate with a corresponding socket of system control unit 126, or vice versa. In other configurations, the connector 222 may be permanently or semi-permanently coupled to the system control unit 126. For example, the connector 222 may be permanently affixed to a housing 446 of the system control unit 126 in a manner such that removal of the connector 222 from the housing 446 may damage either the system control unit 126 or the connector 222 (e.g., permanent fasteners, adhesive, tamper-proof screws etc.). Thus, in some configurations, the connector 222 cannot be removed from the system control unit 126 without damaging the system control unit 126 or the connector 222. The authentication module 242 of the connector 222 may be communicatively coupled to system control unit 126 via the connector 222.

The connector 224 may be configured to couple to the X-ray assembly 114 and/or the authentication module 244. The connector 224 may mechanically and communicatively couple the communication channel 220 to the X-ray tube 452 of the X-ray assembly 114. In some configurations, the connector 224 may be permanently or semi-permanently coupled to the X-ray assembly 114 and/or the authentication module 244. For example, the connector 224 may be permanently affixed to a housing of the authentication module 244. In another example, the connector 224 may be permanently affixed to a housing 412 of the X-ray tube 452. The connector 224 may be permanently coupled in a manner such that removal of the connector 224 from the housing 412 may damage either the X-ray tube 452 or the connector 224 (e.g., permanent fasteners, adhesive, tamper-proof screws etc.). Thus, in some configurations, the connector 224 cannot be removed from the X-ray tube 452 without damaging the X-ray tube 452 or the connector 224.

In other configurations, the connector 224 may removably couple to the X-ray assembly 114 and/or the authentication module 244. For example, the connector 224 may include a plug configured to mate with a corresponding socket of the X-ray assembly 114, or vice versa. In another example, the connector 224 may include a plug configured to mate with a corresponding socket of the authentication module 244, or vice versa. The authentication module 244 may be communicatively coupled to the system control unit 126 via the connector 224, the communication link 226, and the connector 222.

As illustrated in FIG. 4, the authentication module 244 is associated with the X-ray assembly 114. Specifically, in this example, the authentication module 244 is mechanically coupled to a housing 412 of the X-ray tube 452. The authentication module 244 may be permanently or semi-permanently (for example, in a manner that permits removal for servicing, replacement, etc.) coupled to the housing 412. In other configurations, the authentication module 244 may be positioned at least partially inside of the housing 412 of the X-ray tube 452. For example, in FIG. 2, the authentication module 244 is shown positioned inside of the housing 248 of the imaging component 204 (corresponding to the X-ray tube 452 and/or the X-ray assembly 114).

In further configurations, the authentication module 244 may be positioned at other portions of the X-ray tube 452 or the system 100. In some embodiments, the authentication module 244 may be included as an integral part of the X-ray tube 452. In other configurations, the authentication module 244 may be a separate component from the X-ray tube 452.

The authentication module 242 and the authentication module 244 may be configured to identify and/or authenticate the X-ray tube 452. For example, the authentication module 242 may authenticate with the X-ray tube 452 via the authentication module 244. In some configurations, authentication may be performed at the system control unit 126. In other configurations, authentication may occur between the authentication module 242 and the authentication module 244.

In other configurations, the authentication module 242 may be associated with the system control unit 126 rather than the communication channel 220. In such configurations, the authentication module 242 may be removably or permanently coupled to the system control unit 126. For example, the authentication module 242 may be removably or permanently coupled to the housing 446. In another example, the authentication module 242 may be at least partially positioned inside of the housing 446 defined by the system control unit 126.

FIG. 4 also illustrates the X-ray source assembly 114 in further detail. As illustrated, the X-ray tube 452 includes an evacuated enclosure 402 disposed within the housing 412. Disposed within the evacuated enclosure 402 is a cathode 404 and an anode assembly 400, which in this embodiment includes a rotating anode 408. In other configurations, the X-ray tube 452 may include other anode configurations, such as a stationary anode.

The anode 408 and cathode 404 are spaced apart from one another and are connected in an electrical circuit that allows for the application of a high voltage potential between them. The cathode 404 includes an electron emitter 420 that is connected to an appropriate power source (e.g., a generator, not shown).

The housing 412 may partially or entirely surround the evacuated enclosure 402. The housing 412 may define or include cooling lines or a cooling chambers (not shown) configured to receive a coolant to manage the temperature of the X-ray tube 452.

During operation of the X-ray tube 452, an electrical current may be supplied to the electron emitter 420 (typically fashioned as a filament) of the cathode. This causes the electrons "e" to be formed on the emitter 420 by thermionic emission. The application of a high voltage differential between the anode 408 and the cathode 404 then causes the electrons "e" to accelerate from the electron emitter 420 toward a focal track 410 that is positioned on the rotating anode 408. The focal track 410 may include, for example, tungsten, rhenium or other material(s) having a high atomic ("high Z") number. As the electrons "e" accelerate, they gain a substantial amount of kinetic energy, and upon striking the rotating focal track 410, some of this kinetic energy is converted into X-rays "x".

The focal track 410 is oriented so that emitted X-rays "x" may pass through a window 406 formed in the evacuated enclosure 402. The window 406 may include an X-ray transmissive material such that the X-rays "x" emitted from the focal track 410 pass through the X-ray tube window 406 and travel to a patient or object. The window 406 may contribute to sealing the vacuum of the evacuated enclosure 402 of the X-ray tube 452 from atmospheric air pressure outside the X-ray tube 452, while permitting X-rays "x" generated by the anode 408 to exit the X-ray tube 452.

As mentioned, the X-ray tube 452 may be a rotating anode type X-ray tube with a rotating anode 408. The anode 408 may be supported by a bearing assembly 414 that permits the anode 408 to rotate. The bearing assembly 414 may include a rotor and bearings (not shown). The rotor may be mechanically coupled to the anode 408 and the bearings may permit the rotor to rotate. A stator (not shown) may induce rotation of the rotor by electromagnetic induction. The stator may be positioned outside of the evacuated enclosure 402 proximate the rotor positioned inside of the evacuated enclosure 402.

Figure 5:
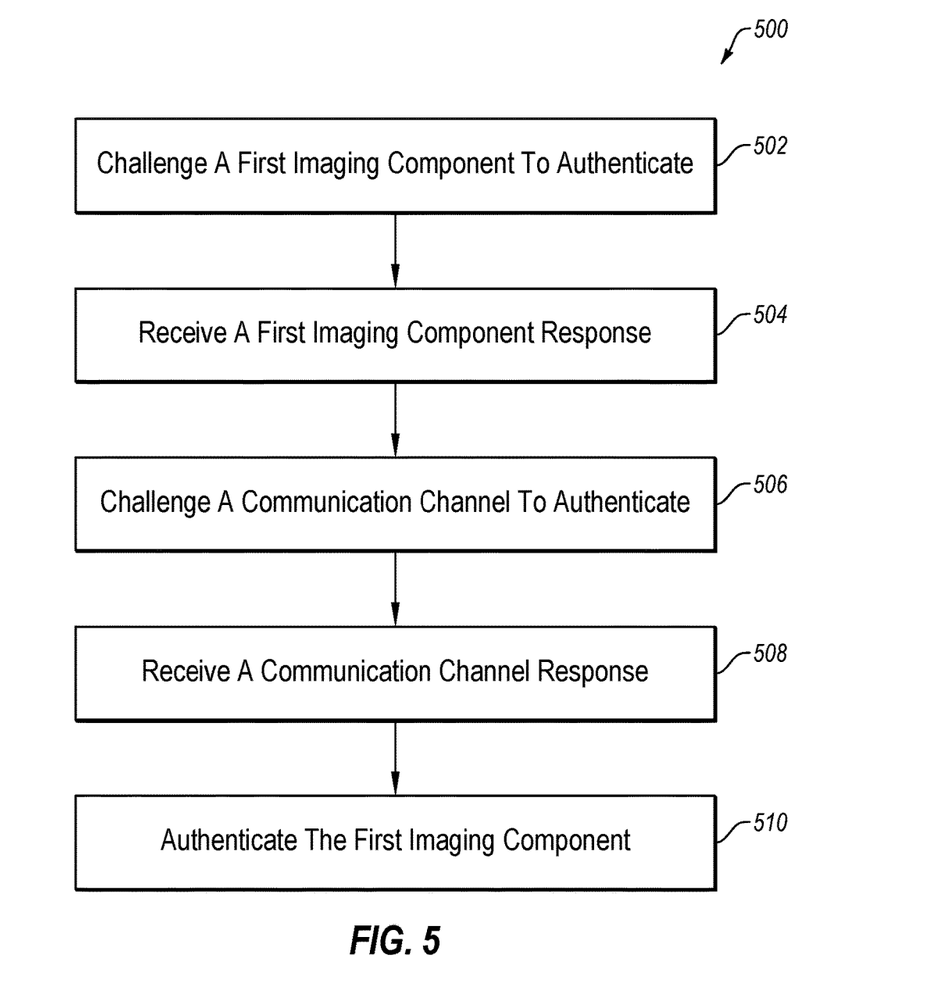
FIG. 5 is a flow chart of an example method.

FIG. 5 is a flow chart of an example method 500, which may be implemented, for example, in the system 100. The method 500 may operatively couple a first imaging component to a second imaging component. For example, the method may be implemented in the system 100 to couple the first imaging component 202 to the second imaging component 204 (see FIG. 2).

The method 500 may begin at block 502, in which a first imaging component may be challenged to authenticate. For example, the imaging component 204 may be challenged to authenticate when the imaging component 202 transmits the challenge 306 to the authentication module 244 associated with the imaging component 204 (see FIG. 2).

At block 504, a first imaging component response may be received as a result of the first imaging component challenge. For example, the imaging component 202 may receive the response 308 from the authentication module 244 of the imaging component 204, as a result of the challenge 306 (see FIG. 2).

At block 506, a communication channel may be challenged to authenticate. The communication channel may be coupled to the first imaging component. For example, the communication channel 220 may be challenged to authenticate when the imaging component 202 transmits the challenge 302 to the authentication module 242 associated with the communication channel 220 (see FIG. 2).

At block 508, a communication channel response may be received as a result of the communication channel challenge. For example, the imaging component 202 may receive the response 304 from the communication channel 220 as a result of the challenge 302 (see FIG. 2).

At block 510, the first imaging component may be authenticated. The first imaging component may be authenticated if the first imaging component response matches the communication channel response. For example, the imaging component 204 may be authenticated with the imaging component 202 if the response 302 matches the response 308. Additionally or alternatively, the first imaging component may fail authentication if the first imaging component response does not match the communication channel response. Furthermore, the first imaging component may fail authentication if the first imaging component response or the communication channel response is not received, for example, after a predetermined time interval passes.

In some configurations of the method 500, the first imaging component may include a controller configured to communicate with and/or operate the second imaging component, and the second imaging component may include an X-ray tube, a generator, and/or an X-ray detector. In some configurations, the first imaging component response may include first imaging component data that uniquely corresponds to the first imaging component. The first imaging component data may include serial number, part number, batch number, lot number, model number, manufacturing date, manufacturing location, country of origin, application code version, and/or bootloader version.

In some configurations of the method 500, the first imaging component response and the communication channel response are received at the second imaging component, and the step of authenticating is performed at the second imaging component.

In some configurations, the method 500 includes encrypting the first imaging component challenge, the first imaging component response, the communication channel challenge and/or the communication channel response. For example, the imaging component 202 may encrypt the challenge 302 prior to transmittal to the authentication module 242 (see FIG. 3). The imaging component 202 may encrypt the challenge 306 prior to transmittal to the authentication module 244. The authentication module 242 may encrypt the response 304 prior to transmittal to the imaging component 202. The authentication module 244 may encrypt the response 308 prior to transmittal to the imaging component 202.

The method 500 may include decrypting the first imaging component challenge, the first imaging component response, the communication channel challenge and/or the communication channel response. For example, authentication module 242 may decrypt the challenge 302 after receiving the encrypted challenge 302 (see FIG. 3). The imaging component 202 may decrypt the response 304 after receiving the encrypted response 304. The authentication module 244 may decrypt the challenge 306 after receiving the encrypted challenge 306. The imaging component 202 may decrypt the response 308 after receiving the encrypted response 308.

In some configurations, the method 500 may include communicating imaging data or control signals over the communication channel after the first imaging component is authenticated. For example, if the first imaging component is successfully authenticated with the second imaging component, imaging data or control signals may be communicated between the first imaging component and the second imaging component over the communication channel.

In some configurations of the method 500, certain data may not be transferred before the first imaging component is authenticated. For example, the second imaging component may be configured to release or transmit data to communicate with and/or operate the first imaging component only after the first imaging component has been authenticated. In another example, the first imaging component may be configured to release or transmit data to the second imaging component only after the first imaging component has been authenticated. Thus, in some configurations, the X-ray imaging system may only be operational after the first imaging component and the second imaging component are authenticated with one another.

The method 500 may include taking steps in response to a successful or failed authentication. The method 500 may include booting up and/or operating normally in response to a successful authentication of the first imaging component. The method 500 may include notifying an operator of the system 100 that a non-approved component is connected to the system in response to a failed authentication. The method 500 may include notifying the manufacturer of the X-ray imaging system or a third party that a non-approved component is connected to the system in response to a failed authentication. The method 500 may include ceasing operation in response to a failed authentication. In some configurations, the method 500 may include preventing the X-ray imaging system from operating in circumstances where at least one component fails to be authenticated.

The terms and words used in the above description and following claims are not limited to the bibliographical meanings, but, are merely used to enable a clear and consistent understanding of the disclosure. It is to be understood that the singular forms "a," "an," and "the" include plural referents unless the context clearly dictates otherwise. Thus, for example, reference to "a component surface" includes reference to one or more of such surfaces.

The embodiments described in this disclosure may include the use of a special purpose or general-purpose computer including various computer hardware or software modules, as discussed in greater detail below.

Embodiments within the scope of this disclosure also include computer-readable media for carrying or having computer-executable instructions or data structures stored thereon. Such computer-readable media can be any available media that can be accessed by a general purpose or special purpose computer. By way of example, and not limitation, such computer-readable media can comprise random-access memory (RAM), read-only memory (ROM), electrically erasable programmable read-only memory (EEPROM), compact disc read-only memory (CD-ROM) or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media.

Computer-executable instructions comprise, for example, instructions and data which cause a general purpose computer, special purpose computer, or special purpose processing device to perform a certain function or group of functions.

As used herein, the term "module" or "component" can refer to software objects or routines that execute on the computing system. The different components and modules described herein may be implemented as objects or processes that execute on the computing system (e.g., as separate threads). While the system and methods described herein may be implemented in software, implementations in hardware or a combination of software and hardware are also possible and contemplated. In this description, a "computer" or "computer system" may be any suitable computing system as previously defined herein, or any module or combination of modules running on a computing system.

For the processes and/or methods disclosed, the functions performed in the processes and methods may be implemented in differing order as may be indicated by context. Furthermore, the outlined steps and operations are only provided as examples, and some of the steps and operations may be optional, combined into fewer steps and operations, or expanded into additional steps and operations.

This disclosure may sometimes illustrate different components contained within, or connected with, different other components. Such depicted architectures are merely exemplary, and many other architectures can be implemented which achieve the same or similar functionality.

Aspects of the present disclosure may be embodied in other forms without departing from its essential characteristics. The described aspects are to be considered in all respects illustrative and not restrictive. The claimed subject matter is indicated by the appended claims rather than by the foregoing description. All changes which come within the meaning and range of equivalency of the claims are to be embraced within their scope.

What is claimed is:

1. A communication channel configured to operatively couple a first imaging component of an X-ray imaging system to a second imaging component of the X-ray imaging system, the communication channel comprising:
   a first connector configured to couple to the first imaging component;
   a second connector configured to couple to the second imaging component; and
   a first authentication module configured to authenticate with the second imaging component via a second authentication module associated with the second imaging component by transmitting a challenge from the first authentication module to the second authentication module associated with the second imaging component and receiving a response at the first authentication module from the second authentication module as a result of the challenge.

2. The communication channel of claim 1, wherein the first imaging component comprises a controller configured to communicate with the second imaging component, and the second imaging component comprises at least one of: an X-ray tube, a generator, and an X-ray detector.

3. The communication channel of claim 1, wherein the first authentication module is at least partially positioned within a housing defined by the first connector.

4. The communication channel of claim 3, further comprising a first tamper avoidance device associated with the first authentication module, the first tamper avoidance device configured to prevent removal of the first authentication module from the first connector.

5. The communication channel of claim 1, further comprising a cable extending between the first connector and the second connector, thereby operatively coupling the first imaging component to the second imaging component.

6. The communication channel of claim 5, wherein the first authentication module is coupled to the cable.

7. The communication channel of claim 1, further comprising a wireless communication link extending between the first connector and the second connector, thereby operatively coupling the first imaging component to the second imaging component.

8. The communication channel of claim 1, further comprising a second tamper avoidance device associated with the second authentication module, the second tamper avoidance device configured to prevent removal of the second authentication module from the second imaging component.

9. The communication channel of claim 1, wherein the first authentication module and the second authentication module implement an authentication protocol that is compliant with at least one of the Advanced Encryption Standard (AES) or the Triple Data Encryption Algorithm (3DES) authentication standard.

10. The communication channel of claim 1, wherein the second authentication module comprises second imaging component data that uniquely corresponds to the second imaging component.

11. The communication channel of claim 10, wherein the second imaging component is an X-ray tube, and the second imaging component data comprises at least one of: serial number, part number, batch number, lot number, model number, manufacturing date, manufacturing location, country of origin, application code version, and bootloader version.

12. The communication channel of claim 1, wherein the first imaging component comprises a controller configured to communicate with the second imaging component, and the second imaging component comprises at least one of: an X-ray tube, a generator, and an X-ray detector.

13. A method of operatively coupling a first imaging component of an X-ray imaging system to a second imaging component of the X-ray imaging system, the method comprising:
   challenging a first imaging component to authenticate;
   receiving a first imaging component response as a result of the first imaging component challenge;
   challenging a communication channel coupled to the first imaging component to authenticate;
   receiving a communication channel response as a result of the communication channel challenge; and
   authenticating the first imaging component if the first imaging component response matches the communication channel response.

14. The method of claim 13, wherein the first imaging component response comprises first imaging component data that uniquely corresponds to the first imaging component.

15. The method of claim 14, wherein the first imaging component data comprises at least one of: serial number, part number, batch number, lot number, model number, manufacturing date, manufacturing location, country of origin, application code version, and bootloader version.

16. The method of claim 13, wherein the first imaging component response and the communication channel response are received at the second imaging component, and the step of authenticating is performed at the second imaging component.

17. The method of claim 16, further comprising:
   encrypting at least one of the first imaging component challenge, the first imaging component response, the communication channel challenge and the communication channel response.

18. The method of claim 17, further comprising:
   decrypting at least one of the first imaging component challenge, the first imaging component response, the communication channel challenge and the communication channel response.

19. The method of claim 13, further comprising:
   communicating imaging data or control signals over the communication channel after the first imaging component is authenticated.

20. A system for authenticating a first imaging component with a second imaging component, the system comprising:
   a first imaging component comprising an authentication module;
   a communication channel communicatively coupling the first imaging component to the second imaging component, the communication channel comprising:
      a first connector configured to be coupled to the first imaging component;
      a second connector configured to be coupled to the second imaging component; and
      a channel authentication module configured to authenticate with the first imaging component authentication module by transmitting a challenge from the channel authentication module to the authentication module of the first imaging component and receiving a response at the channel authentication module from the authentication module of the first imaging component as a result of the challenge.

21. The system of claim 20, wherein the communication channel comprises a cable extending between the first connector and the second connector.

22. The system of claim 21, wherein the channel authentication module is at least partially positioned within a housing formed by the second connector.

23. The system of claim 20, wherein the first imaging component authentication module and the channel authentication module comprise first imaging component data that uniquely corresponds to the first imaging component.

* * * * *

UNITED STATES PATENT AND TRADEMARK OFFICE
CERTIFICATE OF CORRECTION

PATENT NO. : 10,327,730 B2  
APPLICATION NO. : 15/292435  
DATED : June 25, 2019  
INVENTOR(S) : Meiler et al.

It is certified that error appears in the above-identified patent and that said Letters Patent is hereby corrected as shown below:

In the Claims

In Column 20, Line 4, cancel the text beginning with "12. The communication channel of claim 1" to an ending in Column 20, Line 8 "and an X-ray detector.", and insert the following claim:
-- 12. A method of operatively coupling a first imaging component of an X-ray imaging system to a second imaging component of the X-ray imaging system, the method comprising:
challenging a first imaging component to authenticate;
receiving a first imaging component response as a result of the first imaging component challenge;
challenging a communication channel coupled to the first imaging component to authenticate;
receiving a communication channel response as a result of the communication channel challenge; and
authenticating the first imaging component if the first imaging component response matches the communication channel response. --

In Column 20, Line 9, cancel the text beginning with "13. A method of operatively coupling" to an ending in Column 20, Line 22 "channel response.", and insert the following claim:
-- 13. The method of claim 12, wherein the first imaging component comprises a controller configured to communicate with the second imaging component, and the second imaging component comprises at least one of: an X-ray tube, a generator, and an X-ray detector. --

In Column 20, Line 23, please delete "The method of claim 13," and insert -- The method of claim 12, --

In Column 20, Line 32, please delete "The method of claim 13," and insert -- The method of claim 12, --

In Column 20, Line 47, please delete "The method of claim 13," and insert -- The method of claim 12, --

Signed and Sealed this  
Third Day of September, 2019

Andrei Iancu  
*Director of the United States Patent and Trademark Office*